United States Patent
Lee

(10) Patent No.: US 9,386,959 B2
(45) Date of Patent: Jul. 12, 2016

(54) X-RAY GENERATOR, X-RAY DETECTOR AND METHOD FOR TAKING X-RAY IMAGES USING THE SAME

(71) Applicant: Samsung Display Co., Ltd., Yongin, Gyeonggi-do (KR)

(72) Inventor: Tae Ho Lee, Hwaseong-si (KR)

(73) Assignee: Samsung Display Co., Ltd., Gyeonggi-do (KR)

( * ) Notice: Subject to any disclaimer, the term of this patent is extended or adjusted under 35 U.S.C. 154(b) by 398 days.

(21) Appl. No.: 13/797,142

(22) Filed: Mar. 12, 2013

(65) Prior Publication Data

US 2014/0133625 A1     May 15, 2014

(30) Foreign Application Priority Data

Nov. 12, 2012    (KR) .......................... 10-2012-0127593

(51) Int. Cl.
    *A61B 6/00*            (2006.01)

(52) U.S. Cl.
    CPC ............... *A61B 6/465* (2013.01); *A61B 6/5294* (2013.01); *A61B 6/545* (2013.01)

(58) Field of Classification Search
    CPC ..................................................... G01N 23/04
    USPC ....................... 378/62, 205, 207, 94
    See application file for complete search history.

(56) References Cited

U.S. PATENT DOCUMENTS

| | | | |
|---|---|---|---|
| 6,928,145 B2 * | 8/2005 | Kobayashi | G03B 42/02 378/117 |
| 7,581,885 B2 | 9/2009 | Ertel et al. | |
| 8,295,553 B2 * | 10/2012 | Machida | 382/107 |
| 2008/0170665 A1 * | 7/2008 | Marar et al. | 378/91 |
| 2009/0257564 A1 * | 10/2009 | Kito et al. | 378/206 |
| 2013/0230137 A1 * | 9/2013 | Keeve et al. | 378/41 |

FOREIGN PATENT DOCUMENTS

| | | |
|---|---|---|
| KR | 1990-0007542 | 10/1990 |
| KR | 10-2011-0103855 | 9/2011 |
| KR | 10-1146833 | 5/2012 |

\* cited by examiner

*Primary Examiner* — Hoon Song
(74) *Attorney, Agent, or Firm* — Knobbe Martens Olson & Bear LLP

(57) ABSTRACT

An X-ray generation system and an X-ray detection system can be used in a method for taking X-ray images. The X-ray generation system includes an X-ray generator that generates X-rays and emits the generated X-rays to an external device. A three-dimensional (3D) posture information detector generates 3D posture information for the X-ray generator, and a communicator transmits the 3D posture information to the external device.

17 Claims, 7 Drawing Sheets

X-RAY GENERATOR, X-RAY DETECTOR AND METHOD FOR TAKING X-RAY IMAGES USING THE SAME

CROSS-REFERENCE TO RELATED APPLICATIONS

This application claims priority from Korean Patent Application No. 10-2012-0127593 filed on Nov. 12, 2012 in the Korean Intellectual Property Office, the disclosure of which is incorporated herein by reference in its entirety.

BACKGROUND

1. Field

Embodiments of the present invention relate to an X-ray generator, an X-ray detector and a method for taking X-ray images using the same which facilitates a retake of X-ray images taken in the same position and direction of the X-ray generator and the X-ray detector as the previous position and direction.

2. Description of the Related Technology

In general, in order to observe internal tissues of a living organism, X-rays, which are highly efficient in transmitting through a subject, are widely used in the medical industry. The X-rays are irradiated into a living organism and the X-rays transmitted through the subject are detected, thereby accurately observing structures of internal tissues of the living organism.

An X-ray generator and an X-ray detector may be used to take X-ray images. Since conventional X-ray generators and X-ray detectors tended to be much larger than a subject, they were generally placed in X-ray photography rooms of hospitals and users had to visit the hospital to take X-ray images.

However, in recent years, X-ray generators and X-ray detectors have been miniaturized and movable X-ray generators and X-ray detectors have become available. In addition, X-ray generators and X-ray detectors which can be carried by users and by which users can take X-ray images themselves have become available.

When the user take X-ray images while holding the X-ray generator or the X-ray detector for himself/herself, it is difficult to identify a relative positional relationship between the X-ray generator and the X-ray detector. Moreover, when the user intends to perform a retake of X-ray images in the same position and direction as the previous position and direction, in which the X-ray images have previously been taken, it may be difficult to determine whether the position and direction, in which the X-ray generator and the X-ray detector are currently arranged, are identical with the previous position and direction, in which the X-ray images were previously taken.

SUMMARY OF CERTAIN INVENTIVE ASPECTS

Embodiments of the present invention provide an X-ray generation system, an X-ray detection system and a method for taking X-ray images using the same, which can easily identify information on the previous position and direction of the X-ray generation system, in which the X-ray images have previously been taken.

Embodiments of the present invention also provides an X-ray generation system, an X-ray detection system and a method for taking X-ray images using the same, which can easily identify information on the previous position and direction of the X-ray detection system, in which the X-ray images have previously been taken.

Embodiments of the present invention also provides an X-ray generation system, an X-ray detection system and a method for taking X-ray images using the same, which can easily identify a relative positional relationship between the X-ray generation system and the X-ray detection system.

Embodiments of the present invention also provides an X-ray generation system, an X-ray detection system and a method for taking X-ray images using the same, which facilitates a retake of X-ray images taken in the same position and direction of the X-ray generation system and the X-ray detection system as the previous position and direction.

The above and other objects of the present invention will be described in or be apparent from the following description of some embodiments.

According to an aspect of the present invention, there is provided an X-ray generation system comprising an X-ray generator generating X-rays and emitting the generated X-rays to an external device, a three-dimensional (3D) posture information detector generating 3D posture information for the X-ray generator, and a communicator transmitting the 3D posture information to the external device.

According to another aspect of the present invention, there is provided an X-ray detection system comprising an X-ray detector detecting X-rays emitted from an X-ray generator and converting the detected X-rays into X-ray image data, a communicator receiving 3D posture information of the X-ray generator, a 3D posture information detector detecting 3D posture information of the X-ray detector, a data store storing the X-ray image data, the 3D posture information of the X-ray generator and the 3D posture information of the X-ray detector, and an image processor generating images based on the X-ray image data, the 3D posture information of the X-ray generator and the 3D posture information of the X-ray detector and outputting the generated images to the external device.

According to an aspect of the present invention, there is provided a method for taking X-ray images comprising allowing an X-ray detection system to detect a first X-ray emitted from an X-ray generation system, converting the detected first X-ray into first X-ray image data, and storing 3D posture information of the X-ray generation system and 3D posture information of the X-ray detection system together with the first X-ray image data.

According to another aspect of the present invention, there is provided a method for taking X-ray images comprising loading 3D posture information of the X-ray generation system and the stored 3D posture information of the X-ray, corresponding to previously taken X-ray images, receiving current 3D posture information of the X-ray generation system and current 3D posture information of the X-ray detection system, comparing the loaded information with the received information, adjusting the relative position or direction of the X-ray generation system and the X-ray detection system according to the comparison result, allowing the X-ray detection system to detect X-rays emitted from the X-ray generation system, converting the detected X-rays into X-ray image data, and storing current 3D posture information of the X-ray generation system and current 3D posture information of the X-ray detection system together with the X-ray image data.

The 3D posture information detector may measure 3D position and direction of the X-ray generation system.

The 3D posture information detector may include at least one of a gyro sensor, an acceleration sensor, a slope sensor, a geomagnetism sensor, an ultrasonic sensor, an infrared sensor or a camera.

The 3D posture information detector may measure 3D position and direction of the X-ray detector.

The image processor may generate images including at least one of the X-ray image data, the 3D posture information of the X-ray generator and the 3D posture information of the X-ray detector.

The image processor may load the 3D posture information of the X-ray generator and the 3D posture information of the X-ray detector, corresponding to previously taken X-ray images from the data store, receive current 3D posture information of the X-ray generator through the communicator, receive current 3D posture information of the X-ray detector from the 3D posture information detector, compare the loaded information with the received information, and output the comparison result.

The image processor may load information on previous positions and directions of the X-ray generator and the X-ray detector, in which the X-ray images have previously taken.

The image processor may compare the previous position and direction of the X-ray generator with the current position and direction of the X-ray generator, and compare the previous position and direction of the X-ray detector with the current position and direction of the X-ray detector.

The image processor may generate and output images including at least one of information on the previous position and direction of the X-ray generator, information on the previous position and direction of the X-ray detector, information on the current position and direction of the X-ray generator and information on the current position and direction of the X-ray detector.

The image processor may generate and output images including information on whether or not the previous position of the X-ray generator is identical with the current position of the X-ray generator.

The image processor may generate and output images including information on whether or not the previous position of the X-ray detector is identical with the current position of the X-ray detector.

The 3D posture information of the X-ray generator may include information on the position and direction in which the X-ray generator is arranged, and the 3D posture information of the X-ray detector includes information on the position and direction in which the X-ray detector is arranged.

The method for taking X-ray images may further comprise loading the stored 3D posture information of the X-ray generator and the stored 3D posture information of the X-ray detector, receiving current 3D posture information of the X-ray generator and current 3D posture information of the X-ray detector, comparing the loaded information with the received information, and outputting the comparison result.

The method for taking X-ray images may further comprise loading the stored 3D posture information of the X-ray generator and the stored 3D posture information of the X-ray detector, receiving current 3D posture information of the X-ray generator and current 3D posture information of the X-ray detector, comparing the loaded information with the received information, adjusting the relative position or direction of the X-ray generator and the X-ray detector according to the comparison result, allowing the X-ray detector to detect a second X-ray emitted from the X-ray generator, converting the detected second X-ray into second X-ray image data, and storing current 3D posture information of the X-ray generator and current 3D posture information of the X-ray detector together with the second X-ray image data.

BRIEF DESCRIPTION OF THE DRAWINGS

The above and other features and advantages of the present invention will become more apparent by describing in detail certain embodiments thereof with reference to the attached drawings in which.

DETAILED DESCRIPTION OF CERTAIN EMBODIMENTS

Figure 1:
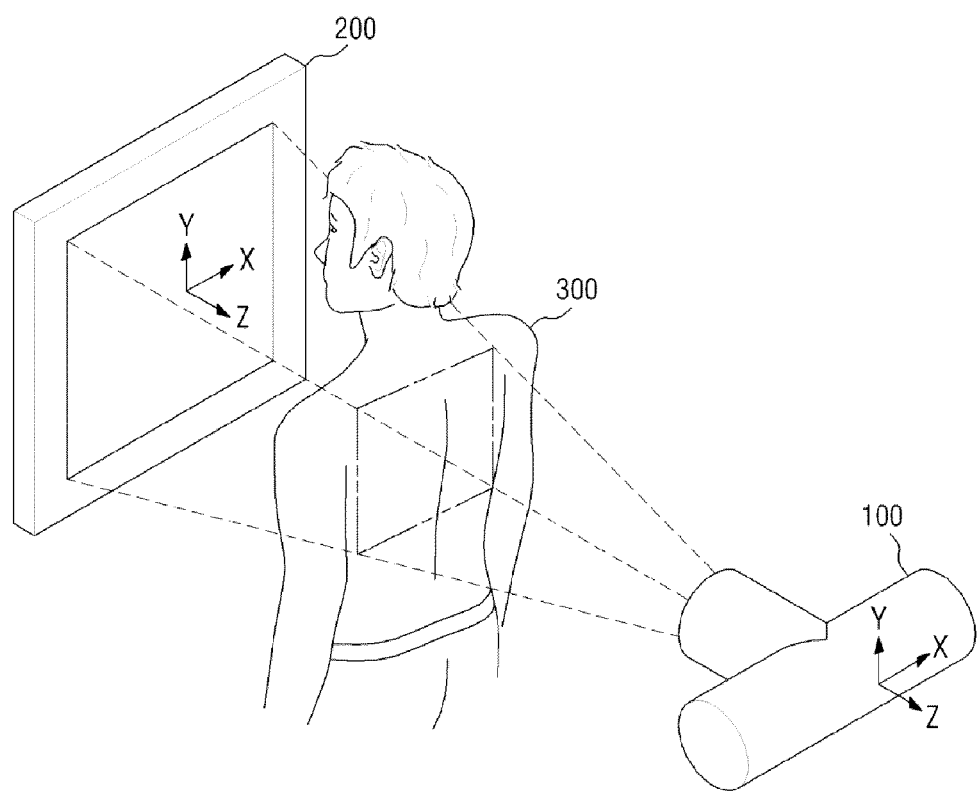
FIG. 1 is a conceptual diagram illustrating X-ray images taken using an X-ray generator and an X-ray detector according to an embodiment of the present invention.

Advantages and features of the present invention and methods of accomplishing the same may be understood more readily by reference to the following detailed description of embodiments and the accompanying drawings. The present invention may, however, be embodied in many different forms and should not be construed as being limited to the embodiments set forth herein. Rather, these embodiments are provided so that this disclosure will be thorough and complete and will fully convey the concept of the invention to those skilled in the art, and the present invention will only be defined by the appended claims. Thus, in some embodiments, well-known structures and devices are not shown in order not to obscure the description of the invention with unnecessary detail. Like numbers generally refer to like elements throughout. In the drawings, the thickness of layers and regions may be exaggerated for clarity.

It will be understood that when an element or layer is referred to as being "on," or "connected to" another element or layer, it can be directly on or connected to the other element or layer or intervening elements or layers may be present. In contrast, when an element is referred to as being "directly on" or "directly connected to" another element or layer, there are no intervening elements or layers present. As used herein, the term "and/or" includes any and all combinations of one or more of the associated listed items.

Spatially relative terms, such as "below," "beneath," "lower," "above," "upper," and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures.

Embodiments described herein will be described referring to plan views and/or cross-sectional views by way of ideal schematic views of the invention. Accordingly, the views may be modified depending on manufacturing technologies and/or tolerances. Therefore, the embodiments of the invention are not limited to those shown in the views, but include modifications in configuration formed on the basis of manufacturing processes. Therefore, regions exemplified in figures have schematic properties and shapes of regions shown in figures exemplify specific shapes of regions of elements and not limit aspects of the invention.

Hereinafter, an X-ray generator, an X-ray detector and a method for taking X-ray images using the same will be described with reference to the accompanying drawings.

FIG. 1 is a conceptual diagram illustrating X-ray images taken using an X-ray generator (100) and an X-ray detector (200) according to an embodiment of the present invention.

Referring to FIG. 1, a user may take X-ray images using the X-ray generator 100 and the X-ray detector 200. For example, as shown in FIG. 1, the user may take X-ray images of parts of his/her own body 300. In addition, the user may also take X-ray images of another person's body parts. Further, the user may also take X-ray images of subjects other than humans.

The X-ray generator 100 may be arranged at an arbitrary position and direction. The X-ray detector 200 may be arranged at an arbitrary position and direction.

X-rays generated from the X-ray generator 100 may be irradiated into a subject 300 positioned between the X-ray generator 100 and the X-ray detector 200. The X-rays may be transmitted through the subject 300. The X-ray detector 200 may detect the X-rays transmitted through the subject 300.

Figure 2:
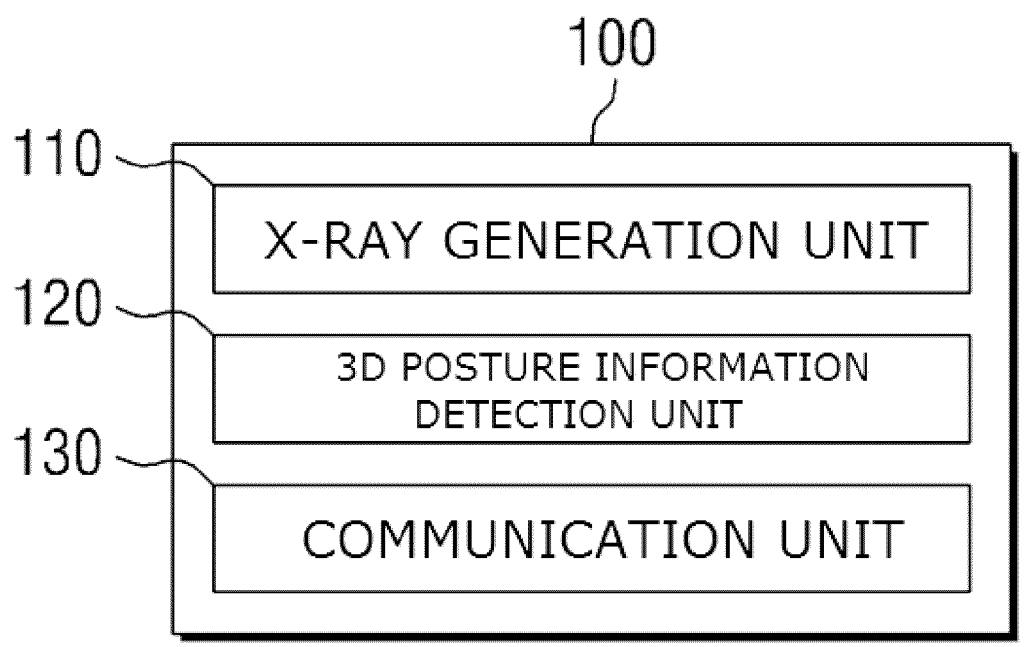
FIG. 2 is a block diagram illustrating a configuration of an X-ray generator according to an embodiment of the present invention.

FIG. 2 is a block diagram illustrating a configuration of an X-ray generator (100) according to an embodiment of the present invention.

Referring to FIG. 2, the X-ray generator 100 according to an embodiment of the present invention may include an X-ray generator 110 generating X-rays and emitting the generated the X-rays to an external device, a 3D posture information detector 120 detecting 3D posture information of the X-ray generator 100, and a communicator 130 transmitting the 3D posture information of the X-ray generator 100 to the external device.

The X-ray generator 110 may generate X-rays. The X-ray generator 110 may generate X-rays using an X-ray tube, a rectifier, and/or a transformer. The X-ray generator 110 may emit the generated X-rays to the external device.

The 3D posture information detector 120 may detect 3D posture information of the X-ray generator 100. The 3D posture information detector 120 may detect, for example, position, direction, slope and/or acceleration of the X-ray generator 100 in a 3D space. The 3D posture information detector 120 may include, for example, at least one of a gyro sensor, an acceleration sensor, a slope sensor, a geomagnetism sensor, an ultrasonic sensor, an infrared sensor or a camera.

Specifically, the 3D posture information detector 120 may detect, for example, position and/or direction of the X-ray generator 100 in a 3D space.

The communicator 130 may transmit the 3D posture information of the X-ray generator 100 detected by the 3D posture information detector 120 to the external device.

The communicator 130 may include a network interface. The network interface may be a near communication module, such as a near field communication (NFC) module, a radio frequency identification (RFID) module, an infrared communication module, a bluetooth module or a ZigBee module. The network interface may be a wireless communication module, such as a Wi-Fi module, a 3G module or a long term evolution (LTE) module. The network interface may be a wired communication module, such as an Ethernet LAN card.

Figure 3:
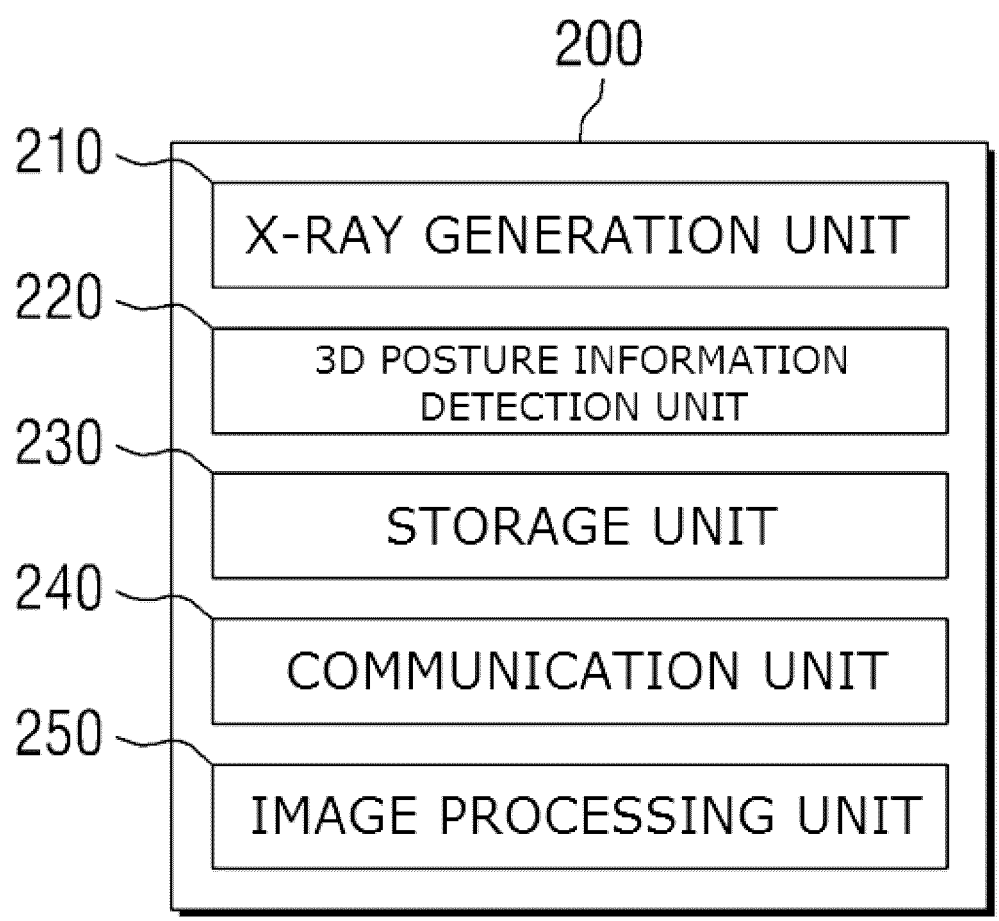
FIG. 3 is a block diagram illustrating a configuration of an X-ray detector according to an embodiment of the present invention.

FIG. 3 is a block diagram illustrating a configuration of an X-ray detector (200) according to an embodiment of the present invention.

Referring to FIG. 3, the X-ray detector 200 according to an embodiment of the present invention may include an X-ray detector 210 detecting X-rays and converting the detected X-rays into X-ray image data, a communicator 240 receiving 3D posture information of the X-ray generator 100, a 3D posture information detector 220 detecting 3D posture information of the X-ray detector 200, a data store 230 storing the X-ray image data, the 3D posture information of the X-ray generator 100 and the 3D posture information of the X-ray detector 200, and an image processor 250 generating images based on the X-ray image data, the 3D posture information of the X-ray generator 100 and the 3D posture information of the X-ray detector 200 and outputting the generated image to the external device.

The X-ray detector 210 may detect X-rays and may convert the detected X-rays into X-ray image data. The X-ray detector 210 may include a scintillator, a thin film transistor (TFT) and/or a photo diode. After the X-rays are received in the scintillator from the external device, the X-rays are transmitted through the scintillator to then be converted into visible light. The visible light may change a charge amount of the photo diode. The charge amount of the photo diode is output by the thin film transistor (TFT), thereby generating the X-ray image data.

The communicator 240 may receive the 3D posture information of the X-ray generator 100 transmitted from the X-ray generator 100. The communicator 240 may include a network interface. The network interface may be a near communication module, such as a near field communication (NFC) module, a radio frequency identification (RFID) module, an infrared communication module, a bluetooth module or a ZigBee module. The network interface may be a wireless communication module, such as a Wi-Fi module, a 3G module or a long term evolution (LTE) module. The network interface may be a wired communication module, such as an Ethernet LAN card.

The 3D posture information detector 220 may detect 3D posture information of the X-ray detector 200. The 3D posture information detector 220 may detect, for example, position, direction, slope and/or acceleration of the X-ray detector 200 in a 3D space.

The 3D posture information detector 220 may include, for example, at least one of a gyro sensor, an acceleration sensor, a slope sensor, a geomagnetism sensor, an ultrasonic sensor, an infrared sensor or a camera.

Specifically, the 3D posture information detector 220 may detect, for example, position or direction of the X-ray detector 200.

The data store 230 may store the X-ray image data, the 3D posture information of the X-ray generator 100 and the 3D posture information of the X-ray detector 200.

The data store 230 may be, for example, a nonvolatile memory such as a flash memory, a hard disk, a magnetic disk or an optical disk. The data store 230 may also be a volatile memory such as a random access memory (RAM), a dynamic RAM (DRAM), or a static RAM (SRAM).

Figure 4:
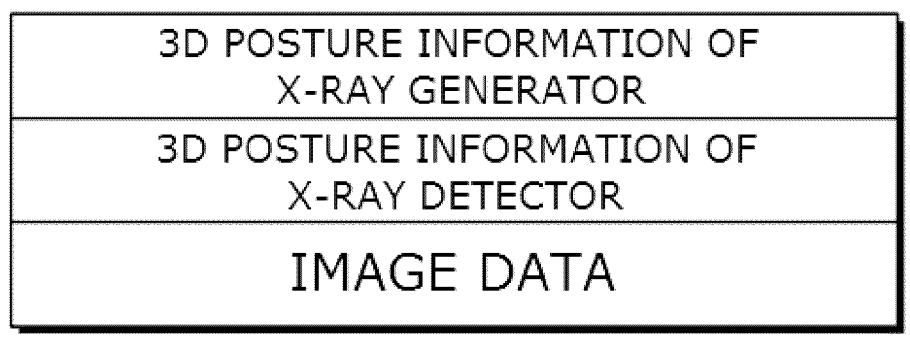
FIG. 4 is a diagram illustrating a format of data stored in a data store of an X-ray detector according to an embodiment of the present invention.

FIG. 4 is a diagram illustrating a format of data stored in a data store (230) of an X-ray detector (200) according to an embodiment of the present invention.

Referring to FIG. 4, the format of data may include three regions: a first region, a second region and a third region. 3D posture information of the X-ray generator 100 may be stored in the first region. 3D posture information of the X-ray detector 200 may be stored in the second region. X-ray image data may be stored in the third region.

Referring again to FIG. 3, the image processor 250 may generate images based on the X-ray image data, the 3D posture information of the X-ray generator 100 and the 3D posture information of the X-ray detector 200. The image processor 250 may generate images including at least one of the X-ray image data, the 3D posture information of the X-ray generator 100 and the 3D posture information of the X-ray detector 200. The image processor 250 may output the generated images to the external device. The output images may be displayed by an external display device.

Figure 5:
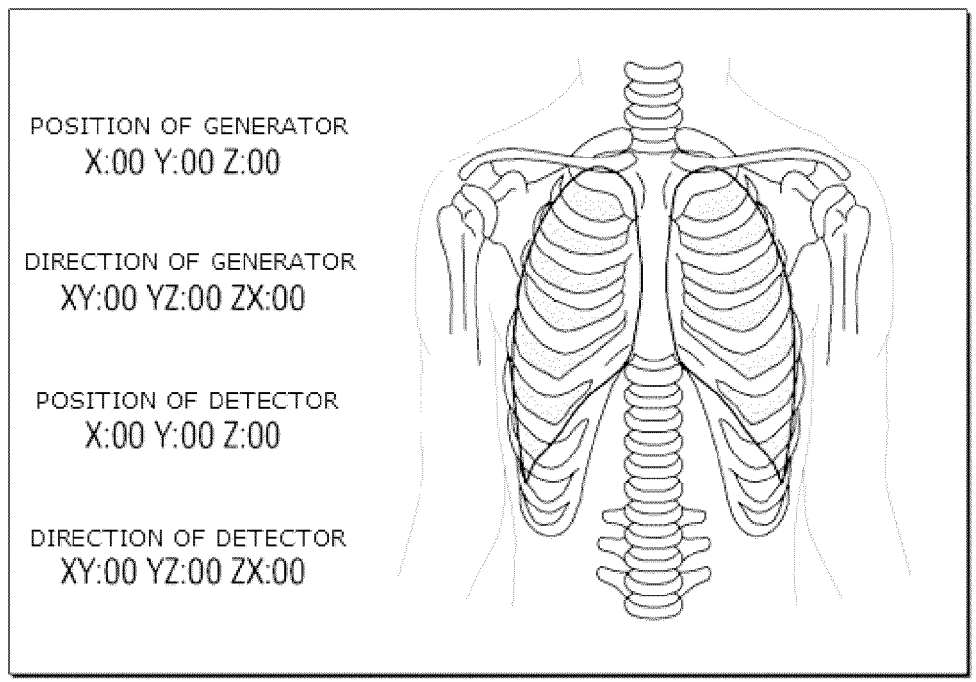
FIG. 5 illustrates a screen on which information on positions and directions of an X-ray generator and an X-ray detector, in which the X-ray images are taken according to an embodiment of the present invention, is output together with X-ray images.

FIG. 5 illustrates a screen on which information on positions and directions of an X-ray generator (100) and an X-ray detector (200), in which the X-ray images are taken according to an embodiment of the present invention, is output together with X-ray images.

Referring to FIG. 5, the X-ray images may be displayed in one region of the screen. In addition, information on the position and direction of the X-ray generator 100 and the position and direction of the X-ray detector 200 may be displayed in another region of the screen.

When the user intends to perform a retake of X-ray images taken in the same position and direction as the previous position and direction, the image processor 250 may load the 3D posture information of the X-ray generator 100 and the 3D posture information of the X-ray detector 200, corresponding to previously taken X-ray images from the data store 230. The image processor 250 may load information on the previous positions and directions of the X-ray generator 100 and the X-ray detector 200.

In addition, the image processor 250 may receive current 3D posture information of the X-ray generator 100 through the communicator 130. In addition, the image processor 250 may receive current 3D posture information of the X-ray detector 200 from the 3D posture information detector 220.

The image processor 250 may compare the loaded information with the received information. The image processor 250 may compare the previous position and direction of the X-ray generator 100 with the current position and direction of the X-ray generator 100. In addition, the image processor 250 may compare the previous position and direction of the X-ray detector 200 with the current position and direction of the X-ray detector 200.

The image processor 250 may output the comparison result. The image processor 250 may generate images including, for example, at least one of information on the previous position or direction of the X-ray generator 100 or the X-ray detector 200 and information on the current position or direction of the X-ray generator 100 or the X-ray detector 200.

The image processor 250 may generate images, further including information on whether or not the previous position of the X-ray generator 100 is identical with the current position of the X-ray generator 100. The image processor 250 may generate images, further including information on whether or not the previous direction of the X-ray generator 100 is identical with the current direction the X-ray generator 100.

The image processor 250 may generate images, further including information on whether or not the previous position of the X-ray detector 200 is identical with the current position of the X-ray detector 200. The image processor 250 may generate images, further including information on whether or not the previous direction of the X-ray detector 200 is identical with the current direction the X-ray detector 200.

The image processor 250 may output the generated images to the external device. The output images may be displayed on an external display device.

A user or an external controller may adjust the positions or directions of the X-ray generator 100 and the X-ray detector 200 according to the comparison result. For example, when the previous positions or directions of the X-ray generator 100 and the X-ray detector 200 are not identical with the current positions or directions of the X-ray generator 100 and the X-ray detector 200, the user or the external controller may adjust the positions or directions of the X-ray generator 100 and the X-ray detector 200, such that the previous positions or directions of the X-ray generator 100 and the X-ray detector 200 become identical with the current positions or directions of the X-ray generator 100 and the X-ray detector 200.

In addition, the user or the external controller may adjust relative positions of the X-ray generator 100 and the X-ray detector 200. Further, the user or the external controller may adjust relative directions of the X-ray generator 100 and the X-ray detector 200. The user or the external controller may adjust only the position or direction of the X-ray generator 100, only the position or direction of the X-ray detector 200, or both of the positions or directions of the X-ray generator 100 and the X-ray detector 200.

After adjusting the relative positions and/or directions of the X-ray generator 100 and the X-ray detector 200, X-ray images may be taken again using the X-ray generator 100 and the X-ray detector 200.

Figure 6:
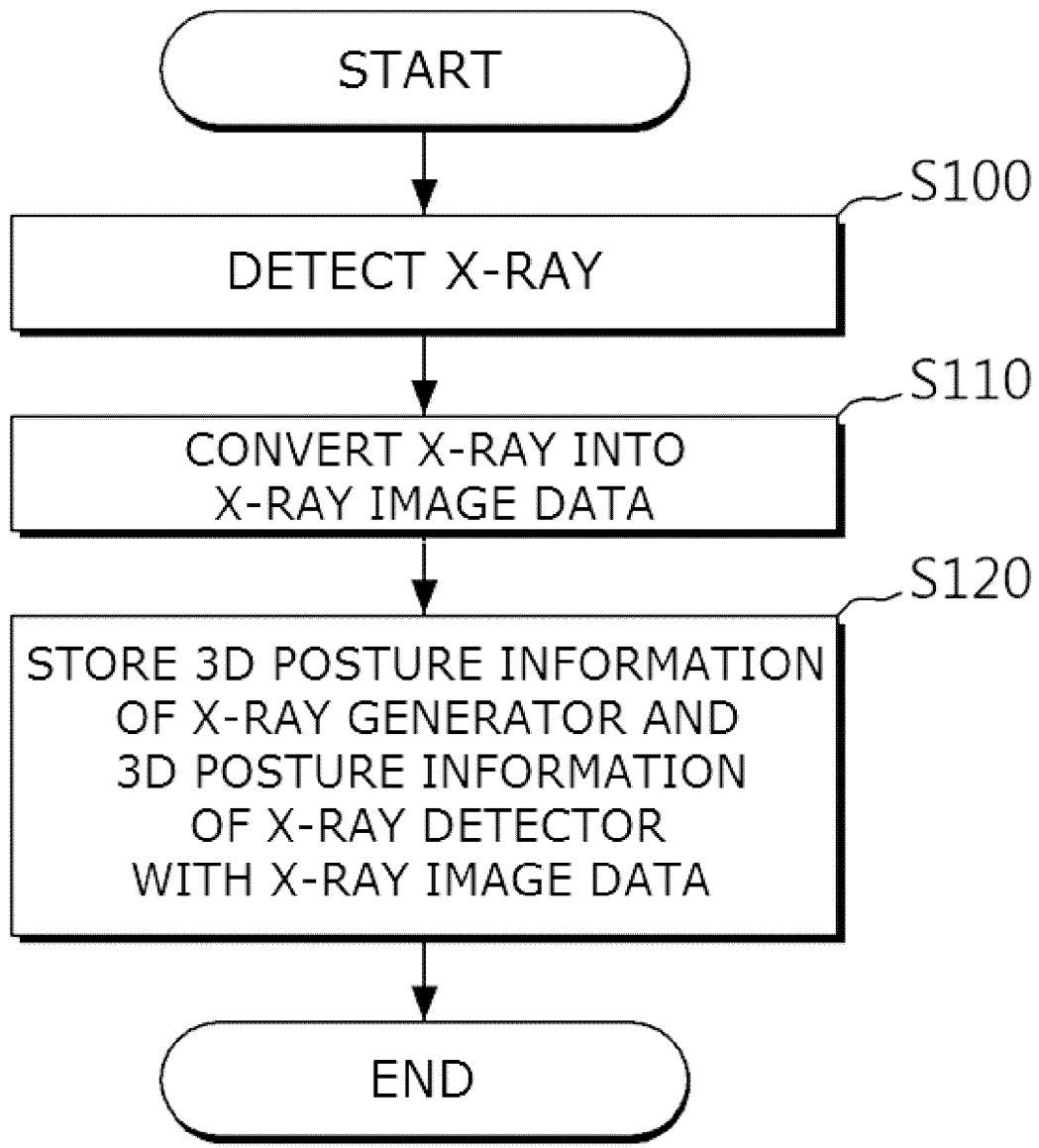
FIG. 6 is a flowchart illustrating an operating process of a method for taking X-ray images according to an embodiment of the present invention.

FIG. 6 is a flowchart illustrating an operating process of a method for taking X-ray images according to an embodiment of the present invention.

Referring to FIG. 6, first, the X-ray detector 200 may detect X-rays emitted from the X-ray generator 100 (S100). Next, the detected X-rays are converted into X-ray image data (S110). Next, the 3D posture information of the X-ray generator 100 and the 3D posture information of the X-ray detector 200 are stored together with the X-ray image data (S120). Information on the position and direction of the X-ray generator 100 and information on the position and direction of the X-ray detector 200 may be stored together with the X-ray image data.

Figure 7:
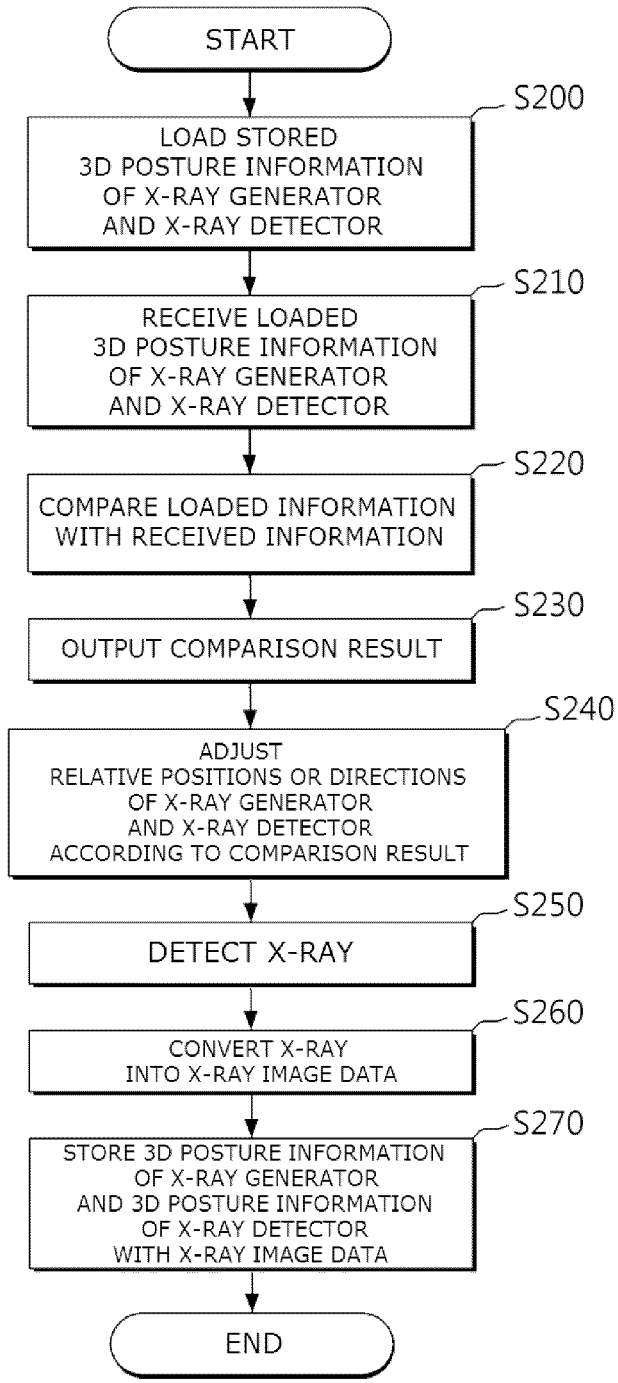
FIG. 7 is a flowchart illustrating an operating process of a method for retaking X-ray images in the same position and direction as those in which the X-ray images have previously been taken.

FIG. 7 is a flowchart illustrating an operating process of a method for retaking X-ray images in the same position and direction as those in which the X-ray images have previously been taken.

Referring to FIG. 7, first, 3D posture information of the X-ray generator 100 and 3D posture information of the X-ray detector 200, corresponding to previously taken X-ray images, are loaded (S200). The previous positions and directions of the X-ray generator 100 and the X-ray detector 200, in which the X-ray images have previously been taken, are loaded.

Next, current 3D posture information of the X-ray generator 100 and current 3D posture information of the X-ray detector 200 are received (S210). Information on the current position and direction of the X-ray generator 100 and information on the current position and direction of the X-ray detector 200 are received.

Next, the loaded information is compared with the received information (S220). The previous position and direction of the X-ray generator 100 are compared with the current previous position and direction of the X-ray generator 100. In addition, the previous position and direction of the X-ray detector 200 are compared with the current previous position and direction of the X-ray detector 200.

Then, the comparison result is output (S230). Images including all of the information on the previous positions and directions of the X-ray generator 100 and the X-ray detector 200 and the current positions and directions of the X-ray generator 100 and the X-ray detector 200 are output.

Images, further including information on whether or not the previous position of the X-ray generator 100 is identical with the current position of the X-ray generator 100, are output. Images, further including information on whether or not the previous direction of the X-ray generator 100 is identical with the current direction of the X-ray generator 100, are output.

Images, further including information on whether or not the previous position of the X-ray detector 200 is identical with the current position of the X-ray detector 200, are output. Images, further including information on whether or not the previous direction of the X-ray detector 200 is identical with the current direction of the X-ray detector 200, are output.

Next, relative positions or directions of the X-ray generator 100 and the X-ray detector 200 are adjusted according to the comparison result (S240). For example, if the loaded information is not identical with the received information and if the previous positions and directions of the X-ray generator 100 and the X-ray detector 200 are not identical with the current positions and directions of the X-ray generator 100 and the X-ray detector 200, the positions and directions of the-ray generator 100 and the X-ray detector 200 may be adjusted. The positions and directions of the X-ray generator 100 and the X-ray detector 200 may be adjusted such that the previous positions and directions of the X-ray generator 100 and the X-ray detector 200 become identical with the current positions and directions of the X-ray generator 100 and the X-ray detector 200.

Only the position or direction of the X-ray generator 100, only the position or direction of the X-ray detector 200, or both of the positions or directions of the X-ray generator 100 and the X-ray detector 200 may be adjusted.

Next, the X-ray detector 200 detects the X-rays emitted from the X-ray generator 100 (S250). Next, the detected X-rays are converted into X-ray image data (S260). Next, the 3D posture information of the X-ray generator 100 and the 3D posture information of the X-ray detector 200 are stored together with the X-ray image data (S270). Information on the current position and direction of the X-ray generator 100 and information on the current position and direction of the X-ray detector 200 are stored together with the X-ray image data.

As described above, according to embodiments of the present invention, the information on the previous position and direction of the X-ray generator 100 may be easily identified. In addition, the information on the previous position and direction of the X-ray detector 200 may be easily identified. In addition, a relative positional relationship between the X-ray generator 100 and the X-ray detector 200 may be easily identified. Further, a retake of X-ray images taken in the same position and direction of the X-ray generator and the X-ray detector as the previous position and direction may be facilitated.

While the present invention has been particularly shown and described with reference to certain embodiments thereof, it will be understood by those of ordinary skill in the art that various changes in form and details may be made therein without departing from the spirit and scope of the present invention as defined by the following claims. It is therefore desired that the present embodiments be considered in all respects as illustrative and not restrictive, reference being made to the appended claims rather than the foregoing description to indicate the scope of the invention.

What is claimed is:

1. An X-ray generation and detection system comprising:
   an X-ray generator generating and emitting X-rays;
   an X-ray detector detecting X-rays emitted from the X-ray generator and converting the detected X-rays into X-ray image data;
   a three-dimensional (3D) posture information detector generating a first 3D position and direction for the X-ray generator and the X-ray detector; and
   a communicator transmitting the 3D position and direction for the X-ray generator and the X-ray detector,
   wherein the X-ray generator and the X-ray detector are configured to be adjusted to a second 3D position and direction based on the first 3D position and direction transmitted by the communicator.

2. The X-ray generation and detection system of claim 1, wherein the 3D posture information detector includes at least one of a gyro sensor, an acceleration sensor, a slope sensor, a geomagnetism sensor, an ultrasonic sensor, an infrared sensor or a camera.

3. The X-ray generation and detection system of claim 1 further comprising:
   a data store storing the X-ray image data, the 3D position and direction of the X-ray generator and the X-ray detector; and
   an image processor generating images based on the X-ray image data, the 3D position and direction of the X-ray generator and the X-ray detector and outputting the generated images.

4. The X-ray generation and detection system of claim 3, wherein the image processor generates images including at least one of the X-ray image data, the 3D position and direction of the X-ray generator and the X-ray detector.

5. The X-ray generation and detection system of claim 3, wherein the image processor is configured to load the first 3D position and direction of the X-ray generator and the X-ray detector, corresponding to previously taken X-ray images from the data store, receive current 3D position and direction of the X-ray generator, receive current 3D position and direction of the X-ray detector from the 3D posture information detector, compare the loaded information with the received information, and output a result of the comparison result.

6. The X-ray generation and detection system of claim 5, wherein the image processor is configured to load information on previous positions and directions of the X-ray generator and the X-ray detector, in which the X-ray images have previously been taken.

7. The X-ray generation and detection system of claim 5, wherein the image processor is configured to compare the previous position and direction of the X-ray generator with the current position and direction of the X-ray generator, and to compare the previous position and direction of the X-ray detector with the current position and direction of the X-ray detector.

8. The X-ray generation and detection system of claim 5, wherein the image processor is configured to generate and output images including at least one of information on the previous position and direction of the X-ray generator, information on the previous position and direction of the X-ray detector, information on the current position and direction of the X-ray generator and information on the current position and direction of the X-ray detector.

9. The X-ray generation and detection system of claim 5, wherein the image processor is configured to generate and output images including information on whether or not the previous position of the X-ray generator is identical with the current position of the X-ray generator.

10. The X-ray generation and detection system of claim 5, wherein the image processor is configured to generate and output images including information on whether or not the previous direction of the X-ray generator is identical with the current direction of the X-ray generator.

11. The X-ray generation and detection system of claim 5, wherein the image processor is configured to generate and output images including information on whether or not the previous position of the X-ray detector is identical with the current position of the X-ray detector.

12. The X-ray generation and detection system of claim 5, wherein the image processor is configured to generate and outputs images including information on whether or not the previous direction of the X-ray detector is identical with the current direction of the X-ray detector.

13. A method for taking X-ray images comprising:
- using an X-ray detector to detect a first X-ray emitted from an X-ray generator;
- converting the detected first X-ray into first X-ray image data;
- storing 3D posture information of the X-ray generator and 3D posture information of the X-ray detector together with the first X-ray image data;
- loading the stored 3D posture information of the X-ray generator and the stored 3D posture information of the X-ray detector;
- receiving current 3D posture information of the X-ray generator and current 3D posture information of the X-ray detector;
- comparing the loaded information with the received information; and
- adjusting the position or direction of the X-ray generator and the X-ray detector according to a result of the comparison.

14. The method of claim 13, wherein the 3D posture information of the X-ray generator includes information on the position and direction in which the X-ray generator is arranged, and the 3D posture information of the X-ray detector includes information on the position and direction in which the X-ray detector is arranged.

15. The method of claim 13, further comprising:
- outputting a result of the comparison.

16. The method of claim 13, further comprising:
- using the X-ray detector to detect a second X-ray emitted from the X-ray generator;
- converting the detected second X-ray into second X-ray image data; and
- storing current 3D posture information of the X-ray generator and current 3D posture information of the X-ray detector together with the second X-ray image data.

17. A method for taking X-ray images comprising:
- loading 3D posture information of an X-ray generator and stored 3D posture information of the X-ray generator, corresponding to previously taken X-ray images;
- receiving current 3D posture information of the X-ray generator and current 3D posture information of an X-ray detector;
- comparing the loaded information with the received information;
- adjusting the position or direction of the X-ray generator and the X-ray detector according to a result of the comparison;
- using the X-ray detector to detect X-rays emitted from the X-ray generator;
- converting the detected X-rays into X-ray image data; and
- storing current 3D posture information of the X-ray generator and current 3D posture information of the X-ray detector together with the X-ray image data.

* * * * *